United States Patent [19]

Frisch

[11] Patent Number: 4,906,423

[45] Date of Patent: Mar. 6, 1990

[54] METHODS FOR FORMING POROUS-SURFACED POLYMERIC BODIES

[75] Inventor: Eldon E. Frisch, Midland, Mich.

[73] Assignee: Dow Corning Wright, Arlington, Tenn.

[21] Appl. No.: 111,889

[22] Filed: Oct. 23, 1987

[51] Int. Cl.$^4$ .............................................. B29C 41/02
[52] U.S. Cl. ...................................... 264/48; 264/134; 264/154; 264/293; 264/317
[58] Field of Search ........ 264/49, 317, 293, DIG. 44, 264/154, 48, 134; 210/500.21, 500.34; 128/334 R; 604/93,94

[56] References Cited

U.S. PATENT DOCUMENTS

| | | | |
|---|---|---|---|
| 2,688,139 | 9/1954 | Jardon | 3/13 |
| 2,996,389 | 8/1961 | Fernhof | 106/41 |
| 3,090,094 | 5/1963 | Schwartzwalder et al. | 25/156 |
| 3,097,930 | 7/1963 | Holland | 25/156 |
| 3,099,067 | 7/1963 | Merriam | 264/344 |
| 3,176,054 | 3/1965 | Einstein et al. | 264/44 |
| 3,198,865 | 8/1965 | Porter | 264/317 |
| 3,350,488 | 10/1967 | Breen | 264/344 |
| 3,547,721 | 12/1970 | Dietzsch | 264/317 |
| 3,562,374 | 2/1971 | Okamoto | 264/344 |
| 3,700,380 | 10/1972 | Kitrilakis | 3/1 |
| 3,716,614 | 2/1973 | Okamoto | 264/344 |
| 3,789,100 | 1/1974 | Kropscott | 264/317 |
| 3,877,080 | 4/1975 | Olcott | 3/1 |
| 3,887,713 | 6/1975 | Rasmussen | 264/129 |
| 3,890,107 | 6/1975 | White et al. | 428/613 |
| 3,890,417 | 6/1975 | Vallance | 264/49 |
| 3,899,556 | 8/1975 | Heide et al. | 264/44 |
| 3,927,164 | 12/1975 | Shimabukuro | 264/134 |
| 3,930,979 | 1/1976 | Vallance | 204/252 |
| 3,980,613 | 9/1976 | Bachot et al. | 264/45.3 |
| 3,992,725 | 11/1976 | Homsy | 3/1 |
| 4,003,818 | 1/1977 | Juillard et al. | 204/296 |
| 4,026,985 | 5/1977 | Rasmussen | 264/129 |
| 4,129,470 | 12/1978 | Homsy | 156/155 |
| 4,182,641 | 1/1980 | Fitts | 264/293 |
| 4,199,864 | 4/1980 | Ashman | 433/175 |
| 4,244,689 | 1/1981 | Ashman | 433/175 |
| 4,281,669 | 8/1981 | MacGregor | 128/784 |
| 4,355,426 | 10/1982 | MacGregor | 3/1.4 |
| 4,374,669 | 2/1983 | MacGregor | 75/208.R |
| 4,439,391 | 3/1984 | Hung | 264/49 |
| 4,459,252 | 7/1984 | MacGregor | 264/46.9 |
| 4,497,074 | 2/1985 | Rey | 264/317 |
| 4,579,700 | 4/1986 | Cavender | 264/46.4 |
| 4,604,762 | 8/1986 | Robinson | 623/1 |
| 4,610,762 | 9/1986 | Birdwell | 264/317 |
| 4,627,836 | 12/1986 | MacGregor | 604/93 |
| 4,652,412 | 3/1987 | Chiulli | 264/49 |
| 4,781,873 | 11/1988 | Ford | 210/500.21 |

*Primary Examiner*—Jay H. Woo
*Assistant Examiner*—Jeremiah F. Durkin, II
*Attorney, Agent, or Firm*—Allan O. Marki

[57] ABSTRACT

A method of making a polymeric body having a porous surface by (a) applying a fluid polymeric composition to a mold surface of a leachable foam having open pores thereon, (b) curing the composition to form the polymeric body, and (c) leaching the foam from the polymeric body with a suitable solvent which does not dissolve the polymeric body. The method is especially suitable for making porous silicone elastomer bodies by using polystyrene foam as the mold material and the method is useful for forming hollow, porous-surfaced polymeric bodies, e.g. mammary and vascular prostheses.

11 Claims, No Drawings

METHODS FOR FORMING POROUS-SURFACED POLYMERIC BODIES

BACKGROUND OF THE INVENTION

The present invention relates to methods for forming porous-surfaced polymeric bodies and particularly to such methods which use leachable foamed materials as the molding surface.

In the medical field, it has been suggested that it is advantageous for some applications to use implantable polymer-based devices having porous surfaces. For example, it has been suggested that vascular prostheses having porous surfaces on the inside aid in keeping blood clots on the surface of the vascular prosthesis and reduce the chances of having the clots break off the vascular wall, enter the bloodstream, and embolize to various parts of the body. It has also been suggested that having a porous outer surface on mammary prostheses reduces the chances of capsular contracture.

U.S. Pat. Nos. 4,604,762 and 4,459,252 disclose methods for forming porous-surfaced prostheses by mixing salt particles or other water-elutable material in with a polymeric composition, allowing the composition to harden, and removing the water-elutable material by leaching with water.

U.S. Pat. No. 4,199,864 discloses a method of fabricating a plastic implant having a porous surface by coating a mold interior with a release agent, sprinkling a layer of water-soluble crystals on the coated surface, adding an acrylic polymer and monomer mixture to fill the mold, heat curing the mixture, and, subsequently, removing the water soluble crystals by leaching.

U.S. Pat. No. 3,700,380 discloses a method of forming blood handling prostheses containing microcavities by applying fibrous, particulate or granular material (such as Nylon, DACRON, or acetate) to the surface which is to contain microcavities, while the surface is soft, causing the surface to set up, and thereafter using a solvent which dissolves the particles.

U.S. Pat. No. 3,899,556 discloses a method of producing porous ceramic prostheses using a framework prepared by partially dissolved and bonded together polystyrene particles with acetone, filling the framework with casting mass and disintegrating the framework with heat.

U.S. Pat. No. 3,090,094 discloses a method of making porous ceramic articles by immersing an open-celled porous element of pliable synthetic or natural organic material in a slurry of ceramic powder and binder, and, subsequently, firing the coated element to vaporize and burn out the porous element. U.S. Pat. No. 3,097,930 discloses a similar method for making a porous refractory material using a sponge, e.g. of polystyrene.

U.S. Pat. No. 2,996,389 discloses a method of making porous ceramic products by mixing bodies of blown or foamed plastic, such as polystyrene, with raw materials used to make ceramics, and, subsequently, volatilizing the plastic material by burning the finished product. Similarly, U.S. Pat. No. 3,176,054 discloses a similar method for making insulating refractories using hollow, spherical, expanded rigid plastic, e.g. polystyrene, beads.

SUMMARY OF THE INVENTION

In view of these methods, there remains a need for a method of making porous-surfaced polymeric bodies that (1) is relatively simple to perform with relatively few steps to perform, (2) does not use fragile water-soluble granules, such as salt, (3) allows for simple control of the pore size, (4) does not require homogeneously dispersing insoluble crystals in the polymeric composition or mixing of viscous compositions, (5) does not require bonding, lamination, or using multiple solutions to make a porous and non-porous dual-layered body, (6) can utilize polymeric dispersions or solutions, (7) can utilize relatively low viscosity compositions, and (8) minimizes polymer-entrapped materials.

The invention disclosed herein provides a method of making a polymeric body having a porous surface comprising the steps of (a) applying a fluid polymeric composition to a mold surface of a leachable foam having open pores thereon, the composition being capable of forming a polymeric body having resistance to a solvent capable of dissolving the foam, (b) forming said composition into a cohesive polymeric body while in contact with the foam, and (c) leaching the foam from the polymeric body with the solvent. The invention also relates to the method wherein the polymeric composition is a silicone elastomer composition, especially one which is dispersed in hexamethyldisiloxane, and the leachable foam is polystyrene. The invention further relates to forming hollow, porous-surfaced polymeric bodies, especially useful for forming mammary and vascular prostheses.

DETAILED DESCRIPTION OF THE INVENTION

Briefly, the invention comprises a method of forming porous-surfaced polymeric bodies by applying a polymeric composition to the surface of a mold of foam material which is shaped to be the mirror image of the desired shape of the polymeric body and has the desired pore size and density. The polymeric composition is then at least partially cured, and the foam material is then extracted from the polymeric composition using a solvent which dissolves the foam, but does not substantially dissolve the polymeric composition, thereby leaving a porous-surfaced polymeric body.

Various polymeric compositions may be used in the method of this invention, so long as the compositions can be in a fluid form that does not dissolve the foam material used as the molding surface. Furthermore, the compositions must be capable of forming a material which does not dissolve with the solvent used for dissolving the foam. Highly suitable compositions are crosslinkable compositions. The compositions may be solventless, in solvent, or in emulsion form. The important consideration for solvent-containing compositions, is that the solvent for the composition cannot be a solvent for the foamed material. The compositions may be those that form rubbers or plastics and may be curable at room-temperature, or with exposure to heat, UV, or electron-beam, etc. with or without partial vacuum. The curing temperature is limited by the temperature that the foam will withstand before losing its shape. For the method of this invention, it is preferred that compositions requiring mild heating be employed to avoid premature gelation of the composition prior to application to the foam.

Suitable polymeric compositions include epoxy-functional resins, vinyl latexes, and silicone compositions. Suitable silicone compositions that may be used in the method include, for example, elastomeric compositions which cure via $\equiv$SiH to $CH_2$=CHSi$\equiv$ addition, in the presence of a catalyst, such as a platinum catalyst. This addition reaction, which is well-known in the silicone art, may be room temperature or heat curing. Preferably, the composition is diluted in a suitable solvent, e.g. hexamethyldisiloxane (DOW CORNING ®200 Fluid, 0.65 cSt.), to prolong curing of the composition and to obtain a desired working viscosity. Hexamethyldisiloxane is an especially good composition solvent when polystyrene is used as the foam material since the hexamethyldisiloxane does not dissolve polystyrene and readily evaporates during air drying. Other volatile silicones that will dissolve uncured silicone elastomer would work in this invention, also. For example, when the silicone composition is a fluorosilicone elastomer dispersion, a suitable solvent would be a fluorosilicone, e.g. di-trifluoropropyltetramethyldisiloxane.

Condensation curable compositions containing siloxanes having ≡SiOH radicals and crosslinkers having ≡SiOR radicals, which are also well-known in the silicone art, could also be used, especially if they were sprayed on from a two-part package, wherein one part is reactive toward the other, so they are not brought into contact with one another until they are applied to the mold surface.

Another type of polymeric composition that would work with polystyrene foam molds are silicone latex compositions. Methods of preparing aqueous, crosslinked polydiorganosiloxane latexes that would be suitable for this invention are described by Huebner and Saam in U.S. Pat. Nos. 4,568,718 and 4,584,341.

Other polymer latex products could work with foam molds such as those of polystyrene, as long as the cured product of the latex is not dissolved with the solvent used to dissolve the foam.

The viscosity of the fluid polymer composition effects the penetration of the composition into the foam cells, the time required to coat a mandrel (if a mandrel is used), and, therefore, the time required for forming the porous-surfaced polymeric body. It is desirable to use a composition having a low enough viscosity to penetrate the foam's pores in the time desired, yet a high enough viscosity to avoid excessive run-off when the composition is applied to a mandrel. Generally, the higher the composition viscosity, the slower its penetration, and the lower the composition viscosity the more applications required to build up a thickness of the polymeric composition. When using relatively thick compositions one could employ the technique of vacuum impregnation which pulls a vacuum on the foam to remove the air contained in the pores, thus ensuring faster penetration of the composition.

For dipping a polystyrene foam mandrel in a silicone dispersion, the preferred viscosity range of the silicone dispersion is from about 200 to about 2000 cps. as measured with a BROOKFIELD viscometer using a #1 spindle and a speed of 10 RPM's. Suitable concentrations of the dispersion range from about 9-15 weight % silcone in hexamethyldisiloxane, with more preferred concentrations ranging from 9 to 10 weight % silicone.

Various foamed materials may be used for the present invention. The foams may have various ratios of open cell to closed cells: however, the foam s surface needs some open cells in order for the polymeric composition to penetrate into the foam to form a porous-surfaced body. If there are no or few open pores on the surface of a foam, one could air-blast the foam or otherwise fracture the cell walls on the outside surface. The resulting pore size and density of the porous surface is controlled by the cell size and density of the foam material employed.

The foams must be leachable by a solvent which does not dissolve the polymeric body. Suitable leachable foams include those foams which are substantially uncrosslinked, for example, polystyrene foam, styrene-containing foams, foamed gelatin, and foamed sugar when used with appropriate polymeric compositions and leaching solvents. Polymeric materials which work well with polystyrene and styrene-containing foams are silicones, epoxies and vinyl latexes. An example of an epoxy coating resin which will work in the invention with polystyrene foam molds is formed from combining the epoxy resin. EPOXICAL S-415 Surface Coat Resin, with the amine hardener, EPOXICAL S-401 Surface Coat Hardener, both available from Plaster Supply House in LaGrange, Ill. The silicone compositions described above are suitable with polystyrene foam molds. Using either foamed gelatin or foamed sugar has the inherent advantage that the foam is leachable with water. When forming products for medical purposes, it is preferred that medical-grade foams be employed.

The foam may be in the form of a mandrel, may be a surface layer on a mandrel made of, e.g. metal, may form a mold itself, or may be any portion of a mold or mandrel, depending on the desired placement of a porous surface. When the foam is on the outside surface of a mandrel or is a mandrel itself, the method is useful for forming hollow polymeric bodies having a porous surface on the inside. If the hollow body can be turned inside out, the porous surface can thereby be moved to the outside surface. When the foam itself forms a mold cavity, the resulting silicone body can be solid with a porous outer surface. A hollow body may also be formed by inserting a solid mold into a foam mold and filling the space between the solid and the foam molds with the polymeric composition.

To prepare foam for use as a molding surface, a preformed piece of foam is shaped into a form which is the mirror image of the desired shape of the polymeric body, and, if necessary, the foam is cleaned and its surface pores are opened. Any method for shaping the foam may be used. e.g., the foam may be shaped while it is being formed, shaped by hand, or by machine. A handle may be inserted into the foam for holding or handling the foam, e.g. when shaping the foam or when using the foam as a mandrel. For secure attachment of any auxiliary tools to the foam, an adhesive or mechanical attachment may be used.

When polystyrene or polystyrene-containing foam is used, the foam is shaped into the desired form, and sanded lightly to open the surface pores more, if desired. Then, preferably, the foam is blown with air or other gas to remove loose foam flakes and dirt to clean and open the pores. I have found that using air at a pressure of about 80 psi to be satisfactory. Then the foam may be washed in the solvent to be used for the dispersion. Epoxy glue may be used for securely attaching any auxiliary tools, such as a handle, to the foam.

Applying the polymeric composition to the mold could be done by pouring the composition into or onto the mold, and, if the mold is a mandrel, by dipping, spraying, rolling, brushing, etc. The thickness of the elastomeric body can be controlled by the amount of composition applied to the mandrel, e.g. by the number of dips and/or the viscosity of the polymeric composition. When it is desired to form a hollow, porous-surfaced polymeric body, generally several applications of the composition to the mandrel are required, the first few applications filling the pores of the foam and the later ones building the non-porous outer layer. Generally, preparing porous-surfaced hollow bodies according to the invention will require more applications of the composition than would non-porous hollow bodies.

There are various ways of improving the penetration of the polymeric composition and reducing air-bubbles at the surface of the molds or mandrels. These ways are carried out, for example, (1) by wetting or soaking the mandrel with the solvent prior to applying the composition if the composition is in solvent, (2) by keeping the mandrel immersed in the composition longer if the mandrel is being dipped in the polymeric composition, and (3) by drawing a slight vacuum on the composition while the composition is being applied to the mold.

For forming hollow, porous-surfaced silicone bodies, dipping polystyrene mandrels in the platinum-curing silicone dispersions mentioned above has been found to be highly suitable. For dipping polystyrene foam mandrels in a 10 weight % silicone dispersion in hexamethyldisiloxane it has been found that best results are achieved when the mandrel remains in the dispersion for about 15 minutes for the first dip, so that the dispersion can thoroughly wet and penetrate the foam and the air bubbles can escape. After several dips, the formation of a non-porous layer becomes evident as the coated mandrel surface changes from dull to glossy in appearance.

The conditions for setting or curing the applied polymeric composition are dictated by the type of composition used. In most cases, the composition needs only to be partially cured to continue with the process and extract the solvent-elutable foam. If the polymeric composition is to be heat cured, the composition must be curable at temperatures mild enough so as not to significantly disturb the characteristics of the foam before the polymeric composition is set. For example, for a particular polystyrene foam, the heat distortion temperature (the temperature at which no distortion by heating alone takes place) may be between 165° and 175° F. Therefore, the initial curing should be kept below 165° F. when using such a polystyrene as the foam.

Once the polymeric composition is at least partially cured, the foam can be extracted with a suitable solvent. The extraction process removes the foam, leaving the porous polymer body intact with pores wherever the foam material was present. Polystyrene foam may be solvent-extracted using ketones, esters, or aliphatic, aromatic, or chlorinated hydrocarbons, such as hexane, toluene, naphtha, xylene, octane, benzene, chloroform, methylchloroform, and methylene chloride. Leaching solvents having up to 16 carbons are preferred for ease of removal from the polymeric body.

Several leaching techniques are known and may be used with or without heating. In some cases, for example, when using polystyrene foam for forming medical devices, care should be taken to remove as much of the foam as possible. Employing a soxhlet-type extractor has been found to work well when making silicone elastomeric bodies for medical use. In cases when the polymeric body is swollen by the extraction solvent, care must be taken with handling the polymeric body to avoid tearing it.

After the foam is dissolved away from the polymeric body, the extraction solvent is removed from the polymeric body. If the polymeric body was only partially cured the curing may then be completed.

The methods of the invention are useful for preparing porous surfaced bodies, and are especially useful for preparing hollow porous-surfaced bodies, e.g. balloon-type bodies, such as mammary prostheses, tissue expanders, drug-releasing implants, or blood storage bags or tubular bodies, such as vascular prostheses.

The porous surface may be further treated, as desired, such as making the surface hydrophilic, and coatings, such as barrier coats, may be applied to any non-porous surface of the polymeric body.

EXAMPLE 1

A silicone elastomer porous-surfaced envelope similar to those used to form mammary prostheses, but smaller, was prepared as follows.

Using a rasp, a 2"×3"×3" block of insulation grade polystyrene foam available from The Dow Chemical Company, Midland, Mich., was shaped into a breast-shaped mandrel. The surfaces were blown with air pressurized to about 80 psi to remove dust and open the first few layers of pores. A rodshaped handle was attached to the mandrel and the mandrel was the dipped into a 12 weight % dispersion in hexamethyldisiloxane of an elastomer composition consisting essentially of a dimethylmethylvinylpolysiloxane gum elastomer base, a dimethylmethylhydrogenpolysiloxane crosslinker, and a platinum catalyst which was mixed just prior to dipping since the pot life of the mixture is limited. The mandrel was allowed to soak until surface bubbling had essentially ceased (approximately 15 minutes), and then the mandrel was withdrawn slowly, and the hexamethyldisiloxane allowed to evaporate. The mandrel was dipped a second time and again soaked until the bubbling ceased. The mandrel was dipped an additional 13 more times, and then the coated mandrel was air dried thoroughly, then placed in a room-temperature oven. The oven temperature was increased to 150° F. at a rate of 10° F. per hour and the polymeric coating allowed to cure at 150° F. for about 1½ to 2 hours. The mandrel was then placed and agitated slightly in a bath of chlorothene and left until the polystyrene dissolved. The remaining polymeric body or envelope was then removed from the chlorothene bath and dried thoroughly. The envelope was then turned inside out and placed in a soxhlet extractor and extracted with chlorothene for 8 hours with the extractor operating at a reflux rate of approximately 4 cycles per hour.

The hole was then patched with a piece of porous-surfaced elastomer and then the envelope was post-cured by placing it in a 350° F. oven for 8 hours, which resulted in a silicone elastomer porous-surfaced envelope.

EXAMPLE 2

In this example, a silicone elastomer tube 1" in diameter and 3½" long having a porous inner surface was prepared by a similar method as described in Example 1. A rod-shaped polystyrene foam mandrel was dipped 15 times in a 10 weight % dispersion in hexamethyldisiloxane of the silicone elastomer composition of Example 1. The silicone composition was then cured, the polystyrene removed with chlorothene, and the silicone post-cured to result in a silicone elastomer tube having a wall thickness of 0.020 inches and a porous inner surface.

EXAMPLE 3

In this example, a two-part liquid epoxy consisting of EPOXICAL S-415 Surface Coat Resin and EPOXI- CAL S-401 Surface Coat Hardener, both available from Plaster Supply House in LaGrange, Illinois, was coated on a piece of insulation grade polystyrene foam supplied by The Dow Chemical Company, Midland, Mich., and allowed to cure. The polystyrene foam was then dissolved with chlorothene and the remaining epoxy resin had a porous surface.

These and other variations of the present invention may be made which fall within the scope of the appended claims even though such variations were not specifically discussed above.

That which is claimed is:

1. A method of making a hollow polymeric implantable prosthetic body having a porous surface contiguous with a fluid-tight non-porous layer comprising
   (a) applying a curable fluid polymeric composition to substantially the entire outside surface of a leachable foam surfaced mandrel, said foam having open pores thereon, until said composition enters the open pores and some of said composition forms a continuous overcoat layer enveloping substantially the entire mandrel said composition capable of forming a polymeric body having resistance to a first solvent,
   (b) forming said composition into a cohesive polymeric body while said composition is in contact with said foam, and
   (c) leaching the foam from the polymeric body with said first solvent to form a hollow body having a porous inner surface integral with a non-porous outer surface.

2. The method as claimed in claim 1 wherein the polymeric composition is dispersed in a second solvent.

3. The method as claimed in claim 1 wherein the polymeric composition is a silicone elastomer composition.

4. The method as claimed in claim 3 wherein said silicone elastomer composition is dispersed in hexamethyldisiloxane.

5. The method as claimed in claim 1 wherein the foam is a polymeric foam.

6. The method as claimed in claim 5 wherein the foam is formed of a styrene-containing polymer.

7. The method as claimed in claim 6 wherein the foam is formed of polystyrene.

8. The method as claimed in claim 7 wherein said first solvent is selected from the group consisting of aliphatic, aromatic, and chlorinated hydrocarbons.

9. A method of forming a hollow silicone envelope for an implantable prosthesis having a porous outer surface and a non-porous inner layer comprising
   (a) applying a fluid crosslinkable silicone elastomeric composition to substantially the outside surface of a mandrel having a handle, said outside mandrel surface being formed of a polystyrene foam having open pores thereon, until at least some of said silicone composition enters at least some of the open pores and some of said composition forms a non-porous overcoat layer enveloping substantially the entire mandrel
   (b) at least partially crosslinking said silicone composition while said composition is in contact with said foam and the overcoat layer of said composition forms a continuous non-porous layer to form a cohesive crosslinked body.
   (c) leaching the foam from the crosslinked body with a first solvent to form a hollow elastomeric body having a porous inner layer integral with a non-porous outer layer with a hole through the body where the handle was inserted, and
   (d) inverting said hollow elastomeric body so that the porous surface faces outwardly.

10. A method of forming a fluid tight hollow implantable vascular prosthesis having a porous inner surface and a non-porous outer layer comprising:
    (a) applying a fluid crosslinkable silicone elastomer composition to the outside surface of a rod-shaped mandrel, said outside mandrel surface being formed of a polystyrene foam having open pores thereon, until at least some of said silicone composition enters at least some of the open pores and some of said composition forms a non-porous overcoat layer enveloping said mandrel, and
    (b) at least partially crosslinking said silicone composition while part of said composition is in contact with said foam to form a cohesive crosslinked body,
    (c) leaching the foam from the crosslinked body with a first solvent to form a hollow elastomeric body having an interior porous surface integral with a non-porous exterior layer.

11. A method as claimed in claim 1 further comprising the step of opening some of the pores of said mold surface, prior to step (a).

* * * * *